(12) United States Patent  (10) Patent No.: US 8,755,489 B2
Lavi et al.  (45) Date of Patent: Jun. 17, 2014

(54) TELETHERAPY LOCATION AND DOSE DISTRIBUTION CONTROL SYSTEM AND METHOD

(75) Inventors: Guy Lavi, Mishmeret (IL); Michael Marash, Rishon Le'tzion (IL)

(73) Assignee: P-Cure, Ltd., Lod (IL)

( * ) Notice: Subject to any disclaimer, the term of this patent is extended or adjusted under 35 U.S.C. 154(b) by 424 days.

(21) Appl. No.: 13/294,195

(22) Filed: Nov. 11, 2011

(65) Prior Publication Data
US 2012/0123183 A1  May 17, 2012

Related U.S. Application Data

(60) Provisional application No. 61/412,401, filed on Nov. 11, 2010.

(51) Int. Cl.
*A61N 5/10* (2006.01)
(52) U.S. Cl.
USPC .............................................. 378/65; 378/207
(58) Field of Classification Search
CPC .................... A61N 5/1049; A61N 2005/1061; A61N 2005/1062; A61N 5/1067; A61N 5/1069; A61N 5/1037; A61N 2005/1054; A61N 2005/1059
USPC .................................................. 378/65, 207
See application file for complete search history.

(56) References Cited

U.S. PATENT DOCUMENTS

| 4,385,634 A | 5/1983 | Bowen |
| 4,618,133 A | 10/1986 | Siczek |
| 4,870,287 A | 9/1989 | Cole et al. |
| 5,013,018 A | 5/1991 | Sicek et al. |
| 5,036,530 A | 7/1991 | DiGiovanna et al. |
| 5,039,867 A | 8/1991 | Nishihara et al. |

(Continued)

FOREIGN PATENT DOCUMENTS

| EP | 0776637 A1 | 6/1997 |
| JP | 3075071 A | 3/1991 |

(Continued)

OTHER PUBLICATIONS

M.M. Kats; "Planar System Replacing Gantry for Protons and Carbon Ion Beams Transportation"; Proceedings of the Sixth European Particle Accelerator Conference (EPAC'98), pp. 2362-2364.

(Continued)

*Primary Examiner* — Hoon Song
(74) *Attorney, Agent, or Firm* — Simon Kahn

(57) ABSTRACT

A method of adjusting an irradiation treatment plan, the plan constituted of: obtaining a plurality of reference scans of a target tissue over a breathing cycle; obtaining a pre-treatment scan of the target tissue; identifying the reference scan whose phase is consonant with the obtained pre-treatment scan; computing at least one motion vector field between the identified reference scan and another of the plurality of reference scans different from the identified reference scan; applying the at least one computed motion vector field to one of the obtained pre-treatment scan and the another of the plurality of reference scans so as to obtain at least one synthetic scan whose phase is consonant with the other of the obtained pre-treatment scan and the another of the plurality of reference scans; and adjusting one of an irradiation dose, irradiation angle and irradiation positioning responsive to the at least one synthetic scan.

15 Claims, 2 Drawing Sheets

(56) References Cited

U.S. PATENT DOCUMENTS

| | | |
|---|---|---|
| 5,247,556 A | 9/1993 | Eckert et al. |
| 5,250,019 A | 10/1993 | McGinley |
| 5,398,356 A | 3/1995 | Pfleger |
| 5,574,763 A | 11/1996 | Dehner |
| 5,668,371 A | 9/1997 | Deasy et al. |
| 5,774,915 A | 7/1998 | Scott et al. |
| 5,778,467 A | 7/1998 | Scott et al. |
| 5,784,734 A | 7/1998 | Scott et al. |
| 5,794,586 A | 8/1998 | Oda et al. |
| 5,851,182 A | 12/1998 | Sahadevan |
| 5,879,281 A | 3/1999 | Ein-Gal |
| 5,983,424 A | 11/1999 | Naslund |
| 6,094,760 A | 8/2000 | Nonaka et al. |
| 6,295,671 B1 | 10/2001 | Reesby et al. |
| 6,375,355 B1 | 4/2002 | Fortin |
| 6,386,759 B2 | 5/2002 | Noettling |
| 6,400,791 B1 | 6/2002 | Schwarz |
| 6,502,261 B1 | 1/2003 | Harwood |
| 6,611,700 B1 | 8/2003 | Vilsmeier |
| 6,725,078 B2 | 4/2004 | Bucholz et al. |
| 6,730,921 B2 | 5/2004 | Kraft |
| 6,742,929 B2 | 6/2004 | Horbaschek |
| 6,769,806 B2 | 8/2004 | Moyers |
| 6,780,149 B1 | 8/2004 | Schulte |
| 6,785,360 B1 | 8/2004 | Annis |
| 6,802,564 B2 | 10/2004 | Brockway et al. |
| 6,814,694 B1 | 11/2004 | Pedroni |
| 6,828,792 B1 | 12/2004 | Danby et al. |
| 6,865,253 B2 | 3/2005 | Blumhofer et al. |
| 6,865,411 B2 | 3/2005 | Erbel et al. |
| 6,894,300 B2 | 5/2005 | Reimoser et al. |
| 6,986,179 B2 | 1/2006 | Varadharajulu et al. |
| 7,000,271 B2 | 2/2006 | Varadharajulu et al. |
| 7,003,070 B1 | 2/2006 | Chen et al. |
| 7,020,232 B2 | 3/2006 | Rand et al. |
| 7,062,007 B2 | 6/2006 | Morita |
| 7,137,160 B2 | 11/2006 | Hand et al. |
| 7,154,991 B2 | 12/2006 | Earnst et al. |
| 7,173,265 B2 | 2/2007 | Miller et al. |
| 7,212,608 B2 | 5/2007 | Nagamine et al. |
| 7,215,167 B1 | 5/2007 | Hassun |
| 7,412,311 B2 | 8/2008 | Georgi et al. |
| 7,570,738 B2 * | 8/2009 | Khamene et al. ............ 378/65 |
| 7,640,607 B2 | 1/2010 | Guertin et al. |
| 7,686,509 B1 | 3/2010 | Fleig et al. |
| 7,847,275 B2 | 12/2010 | Lifshitz et al. |
| 2001/0043671 A1 | 11/2001 | Grass et al. |
| 2002/0057758 A1 | 5/2002 | Stark |
| 2002/0095722 A1 | 7/2002 | Korver, II et al. |
| 2003/0058993 A1 | 3/2003 | Bohn |
| 2003/0072416 A1 | 4/2003 | Rasche et al. |
| 2003/0078523 A1 | 4/2003 | Burkhardt et al. |
| 2003/0164459 A1 | 9/2003 | Schardt et al. |
| 2004/0013239 A1 | 1/2004 | Gregerson et al. |
| 2004/0042583 A1 | 3/2004 | Wackerle et al. |
| 2004/0102698 A1 | 5/2004 | Vilsmeier et al. |
| 2004/0125920 A1 | 7/2004 | Zaiki |
| 2004/0162457 A1 | 8/2004 | Maggiore et al. |
| 2004/0172758 A1 | 9/2004 | Alakkat |
| 2004/0199072 A1 | 10/2004 | Sprouse et al. |
| 2004/0240626 A1 | 12/2004 | Moyers |
| 2005/0065675 A1 | 3/2005 | Georgi et al. |
| 2005/0096515 A1 | 5/2005 | Geng |
| 2005/0138732 A1 | 6/2005 | Erbel et al. |
| 2005/0222505 A1 | 10/2005 | Damadian et al. |
| 2005/0228255 A1 | 10/2005 | Saracen et al. |
| 2005/0234327 A1 | 10/2005 | Saracen et al. |
| 2005/0281374 A1 | 12/2005 | Cheng et al. |
| 2006/0002511 A1 | 1/2006 | Miller et al. |
| 2006/0042009 A1 | 3/2006 | Somasundaram et al. |
| 2006/0050848 A1 | 3/2006 | Vilsmeier et al. |
| 2006/0106301 A1 | 5/2006 | Kats |
| 2006/0262898 A1 | 11/2006 | Partain et al. |
| 2007/0003010 A1 | 1/2007 | Guertin et al. |
| 2007/0003123 A1 | 1/2007 | Fu et al. |
| 2007/0041499 A1 | 2/2007 | Lu et al. |
| 2007/0053491 A1 * | 3/2007 | Schildkraut et al. ............ 378/65 |
| 2008/0086816 A1 | 4/2008 | Farooqui |
| 2008/0292053 A1 | 11/2008 | Marash et al. |
| 2009/0074140 A1 | 3/2009 | Ein-Gal |
| 2009/0087124 A1 | 4/2009 | Nord et al. |
| 2009/0149735 A1 | 6/2009 | Fallone et al. |
| 2009/0154645 A1 | 6/2009 | Lifshitz et al. |
| 2009/0168960 A1 | 7/2009 | Jongen et al. |
| 2009/0200483 A1 | 8/2009 | Gall et al. |
| 2009/0217456 A1 | 9/2009 | Lempen et al. |

FOREIGN PATENT DOCUMENTS

| | | |
|---|---|---|
| JP | 8229145 A | 9/1996 |
| JP | 2001095932 A | 4/2001 |
| JP | 2001161839 A | 6/2001 |
| WO | 94/10908 A2 | 5/1994 |
| WO | 98/18523 A1 | 5/1998 |
| WO | 99/53997 A1 | 10/1999 |
| WO | 03/059433 A2 | 7/2003 |
| WO | 03/070101 A1 | 8/2003 |
| WO | 2004/010381 A1 | 1/2004 |
| WO | 2005/018734 A2 | 3/2005 |
| WO | 2005/024721 A2 | 3/2005 |
| WO | 2007/012649 A1 | 2/2007 |
| WO | 2007/017211 A2 | 2/2007 |
| WO | 2007/062788 A1 | 6/2007 |

OTHER PUBLICATIONS

Kamada et al., "A horizontal CT system dedicated to heavy-ion beam treatment", Radiotherapy and Oncology 50, 1999, pp. 235-237.

D. Larose, "Iterative X-Ray/CT Registration Using Accelerated Volume Rendering", Carnegie Mellon University, Pittsburgh, PA, USA, May 2001.

R. Schulte, "Proton Computed Tomography for Clinical Applications", Loma Linda University, Loma Linda CA, USA, Jan. 10, 2002.

Petterson et al., "Proton Radiography Studies for Proton CT", Loma Linda University, Loma Linda, CA, USA, Nov. 26, 2006.

Written Opinion of the International Searching Authority for PCT application PCT/IL2013/050798 from the Israel Patent Office, of mailing date Jan. 30, 2014.

* cited by examiner

TELETHERAPY LOCATION AND DOSE DISTRIBUTION CONTROL SYSTEM AND METHOD

BACKGROUND OF THE INVENTION

The invention relates generally to the field of teletherapy and in particular to a system and method for identifying morphological changes in a target tissue.

Teletherapy is defined as a treatment methodology in which an irradiation source is at a distance from the body to be treated. X-rays and electron beams have long been used in teletherapy to treat various cancers. Unfortunately, X-rays and electron beams exhibit a linear energy transfer approaching an exponential attenuation function, and are therefore of minimal use for deeply embedded growths. Recently, the use of heavy particles, particularly hadrons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadron's path. As a result of this effect, increased energy can be directed at an embedded growth as compared to X-rays and electron beams, which particularly harm intervening tissues. While the term hadrons include a wide range of particles, practically, protons and various ions are most widely used in teletherapy.

Treatment planning and follow up is a critical factor in teletherapy so as to accurately determine the appropriate dose distribution for a target tissue, while causing minimal damage to adjacent tissues. In certain cases, such as where the target tissue is in the chest cavity, a series of scans of the target tissue and surrounding area are taken, to develop a four dimensional image of the target tissue area. In particular the four dimensional image represents a series of three dimensional images over the complete breathing cycle, with each scan thus representing a particular phase of the breathing cycle. The scans may comprise x-ray scans, computerized tomography (CT) scans, positron emission tomography (PET) scans, or ultrasound (US) scans, without limitation. A treatment plan is then developed in relation to a single one of the plurality of phase scans, i.e. while all of the scans may be viewed and utilized, the treatment plan is developed and described in relation to a single one of the plurality of scans. This particular one of the scans is denoted hereinafter the treatment plan phase scan.

Irradiation of the target tissue, in the case of organs whose position vary over the breathing cycle, may be performed by gating the irradiation to occur only during the portion of the breathing phase consonant with the phase of the treatment plan phase scan. Alternatively, irradiation may be performed continuously over the entire breathing cycle, with the treatment plan taking into account movement of the target tissue over the breathing cycle.

Pre-treatment imaging is an important part of teletherapy and is particularly important in obtaining precise location information of the patient as well as updated information regarding the diseased tissue to be irradiated. Location information of the patient is required for accurate positioning of the patient in relation to the irradiation beam, and updated morphological information is used to update the dose distribution determined at the treatment planning stage.

Prior art methods of pre-treatment imaging exist based on x-ray technology, wherein an x-ray image, or a pair of orthogonal x-ray images, is taken of an immobilized patient in position for irradiation. The x-ray image, or a pair of orthogonal images, is compared with synthetic x-ray images derived from a reference computerized tomography (CT) scan for which the initial treatment plan is described, and any location adjustments are performed. The synthetic x-ray image is often called a digital reconstructed radiograph (DRR). The pre-treatment x-ray image, or pre-treatment pair of orthogonal x-ray images is compared with the treatment plan phase scan, and thus precise positioning is performed.

Unfortunately, no morphological updates of the treatment planning are taught in the prior art.

SUMMARY OF THE INVENTION

Accordingly, it is a principal object of the present invention to overcome at least some of the disadvantages of present and prior art methods of teletherapy control. In one embodiment this is provided by a teletherapy control system comprising: a teletherapy management server; and an imaging unit in communication with the teletherapy management server. The teletherapy management server is arranged to: obtain a plurality of reference scans of a target area exhibiting a target tissue and typically comprising critical organs, each of the reference scans representing a scan of the target area and the critical organs at a unique phase of a patient breathing cycle, and one of them preferably being identified as a treatment plan phase scan; obtain from the imaging unit a pre-treatment scan of the target area; identify the reference scan of the plurality of reference scans whose breathing cycle phase is consonant with the obtained pre-treatment scan; compute a motion vector field between the identified reference scan and at least one reference scan such as the treatment plan phase scan; and apply the computed motion vector field to the obtained pre-treatment scan to derive a synthetic pre-treatment plan scan whose phase is consonant with the phase of the treatment plan scan. A morphological and dosimetrical analysis is performed on the consonant scans revealing target tissue deformation, and a patient position with respect to the treatment device and a treatment plan are adjusted responsive to any identified target tissue and critical organs deformation.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
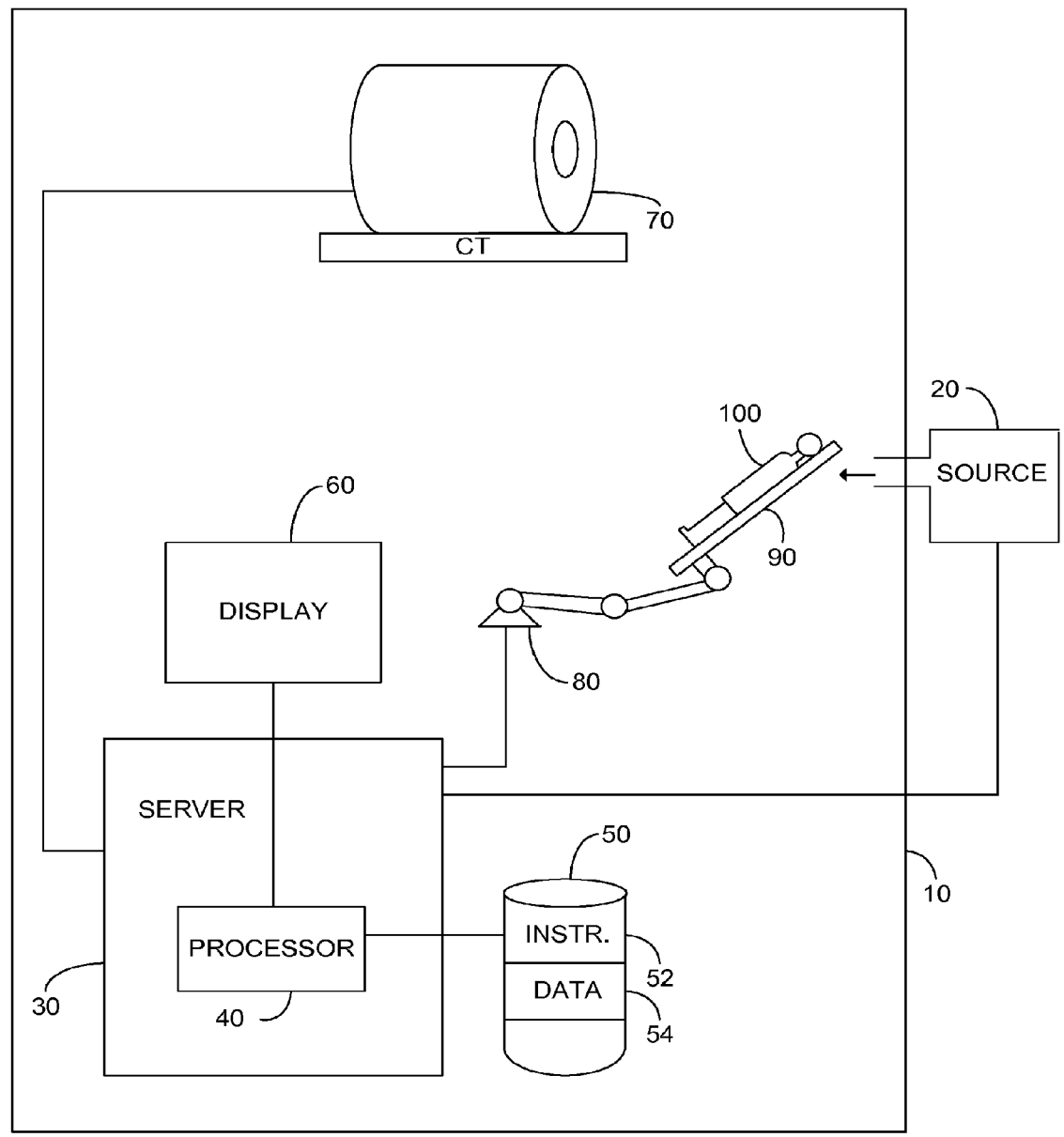
FIG. 1 illustrates a high level block diagram of an exemplary embodiment of an irradiation treatment room comprising a teletherapy management server, an imaging unit and a therapeutic agent source responsive to the teletherapy management server.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting. The term target area as used herein refers to any target area, including without limitation a total patient view.

FIG. 1 illustrates a high level block diagram of an exemplary embodiment of an irradiation treatment room 10 comprising: a therapeutic agent source 20; a teletherapy management server 30 comprising a processor 40; a memory 50; a display 60; a pre-treatment imaging unit 70, illustrated without limitation as a CT unit: and a positioning apparatus 80 in communication with a patient platform 90 having thereon a patient 100. Therapeutic agent source 20 is illustrated as a fixed beam irradiation source, without limitation, and may be replaced with a gantry or other therapeutic agent source without exceeding the scope. Processor 40 is in electronic communication with each of memory 50 and display 60, and is particularly arranged to read computer readable instructions stored on a first portion 52 of memory 50 and read image data received at a treatment planning phase from a second portion 54 of memory 50. Teletherapy management server 30 is in electrical communication with pre-treatment imaging unit 70, with therapeutic agent source 20 and with positioning apparatus 80. Positioning apparatus 80 is arranged to position patient 100 immobilized to patient platform 90 to a particular position in relation to therapeutic agent source 20, the particular position obtained responsive to teletherapy management server 30. Teletherapy management server 30 is illustrated as a single unit, and may be composed of a plurality of processing units in intercommunication as required, without exceeding the scope. Therapeutic agent source 20 is responsive to teletherapy management server 30 to control the dose distribution of the therapeutic agent output there from. Pre-treatment imaging unit 70 is illustrated as being within irradiation treatment room 10, however this is not meant to be limiting in any way, and pre-treatment imaging unit 70 may be external of irradiation treatment room 10 without exceeding the scope.

As described above, irradiation of a target tissue of patient 100 from therapeutic agent source 20 is to be carefully controlled. In the event that a target tissue of patient 100 is subject to motion or other position variance over the breathing cycle, irradiation from therapeutic agent source 20 may be performed by gating irradiation from therapeutic agent source to occur only during the portion of the breathing phase consonant with the phase of the treatment plan phase scan. Alternatively, irradiation from therapeutic agent source 20 may be performed continuously over the entire breathing cycle, with the treatment plan taking into account movement of the target tissue over the breathing cycle.

Figure 2:
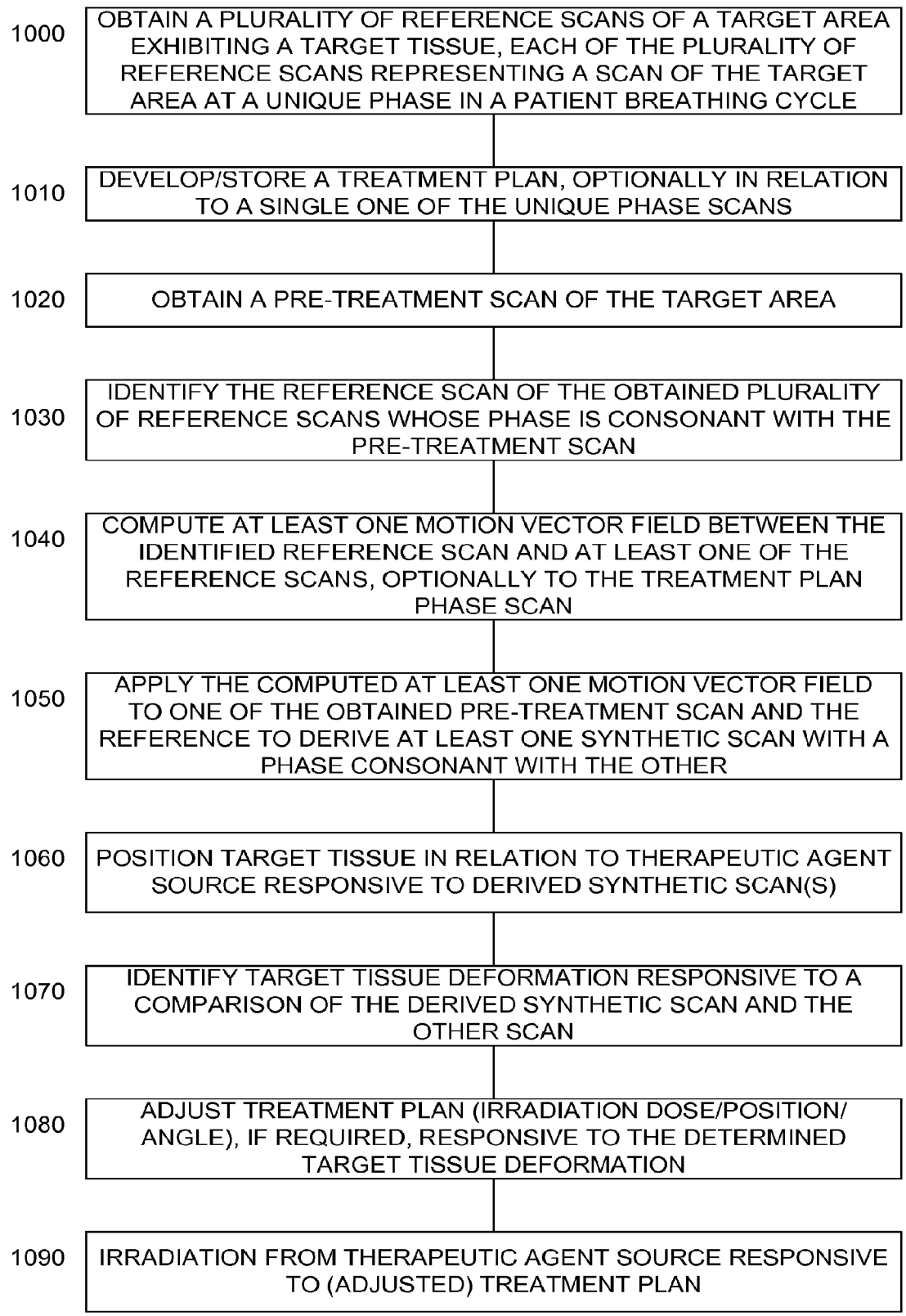
FIG. 2 illustrates a high level flow chart of the method of operation of the teletherapy management server of FIG. 1.

FIG. 2 illustrates a high level flow chart of the method of operation of teletherapy management server 30 of FIG. 1, in accordance with computer readable instructions stored on first portion 52 of memory 50, FIGS. 1 and 2 being taken together.

In operation, and in reference to the stages of FIG. 2, at a reference stage, a plurality of reference image scans of a target area of patient 100 is obtained, the target area comprising a target tissue and typically comprising critical organs, each of the reference images representing a unique phase in a breathing cycle of patient 100, as described in stage 1000. The plurality of reference image scans may be obtained at a planning station, and may be obtained by any of: a plurality of complete CT scans, a cone-beam CT a plurality of x-ray images, a plurality of PET scans and a plurality of US scans, or a combination thereof, without limitation. The plurality of reference image scans is stored on second portion 54 of memory 50.

At a treatment planning stage, as described in stage 1010, a treatment plan is developed responsive to the obtained reference image scans. In one embodiment, the treatment plan is described in relation to a particular one of the obtained image scans over the breathing cycle phases, and denoted the treatment plan phase scan. In another embodiment, the treatment plan takes into account movement of the target tissue over the breathing cycle, and no particular treatment plan phase scan is required to be designated. In one embodiment, the developed treatment plan is stored on memory 50.

In stage 1020, at a pre-treatment stage, a scan of the target area is obtained from pre-treatment imaging unit 70, and communicated to teletherapy management server 30. In stage 1030, the obtained pre-treatment scan of the target area of stage 1020 is compared with the plurality of reference images stored on second portion 54 of memory 50, and utilizing registration points the particular one of the plurality of reference images whose phase in the breathing cycle is consonant with the phase of the obtained pre-treatment scan is identified. Preferably, if the obtained pre-treatment scan is nearly consonant with more than one of the reference image scans, a closest one of the reference image scans is identified as the reference scan having a consonant phase.

In stage 1040, at least one motion vector field is computed between the identified reference scan having the consonant phase and another of the plurality of reference scans of stage 1000, having a phase different from the phase of the identified reference scan. In an embodiment in which a treatment plan phase scan is defined, a vector field is preferably computed between the identified reference scan having the consonant phase and the treatment plan phase scan of stage 1010. In an embodiment in which irradiation is performed over the entire breathing cycle, a plurality of motion vector fields are preferably computed, each associated with a particular one of the plurality of reference scans of stage 1000. In one embodiment all possible motion vector fields are computed in advance and stored in second portion 54 of memory 50. In another embodiment the motion vector field is computed responsive to the identification of stage 1030. The motion vector field is preferably computed in 3 dimensions.

In stage 1050, the at least one computed motion vector field of stage 1040 is applied to one of the obtained pre-treatment scan of stage 1020 and at least one of the respective reference scans of stage 1000 to derive a synthetic, or simulated, scan whose phase is consonant with the other of the obtained pre-treatment scan of stage 1020 and the respective reference scan of stage 1000.

In greater detail, in one embodiment the computed motion vector field of stage 1040 is applied to the obtained pre-treatment scan of stage 1020 to derive a synthetic, or simulated, scan whose phase is consonant with the treatment plan phase scan of stage 1010, thus providing a basis for positioning and/or morphological analysis in comparison with the treatment plan phase scan. In another embodiment the computed motion vector field of stage 1040 is applied to the treatment plan phase scan of stage 1010 to derive a synthetic, or simulated, scan whose phase is consonant with the pre-treatment scan of stage 1020 thus providing a basis for positioning and/or morphological analysis in comparison with the treatment plan phase scan.

In another embodiment, the plurality of computed motion vector fields of stage 1040 are each respectively applied to the obtained pre-treatment scan of stage 1020 to derive a plurality of synthetic, or simulated, scans whose phases are each respectively consonant with one of the obtained plurality of reference scans of stage 1000, thus providing a basis for positioning and/or morphological analysis over the entire breathing cycle. In yet another embodiment, the plurality of computed motion vector fields of stage 1040 are each respectively applied to the plurality of reference scans of stage 1000 to derive a plurality of synthetic, or simulated, scans whose phases are each respectively consonant with the phase of the pre-treatment scan of stage 1020, thus providing a basis for positioning and/or morphological analysis over the entire breathing cycle.

The above computations are described as transformations to at least one of the reference scans or the pre-treatment scan, however this is not meant to be limiting in any way, and the transformations may be to a fixed, or pseudo-point breathing cycle without exceeding the scope.

In stage 1060, positioning of the target tissue of stage 1000 is performed responsive to the derived synthetic scan, or scans, of stage 1050. In particular, positioning apparatus 80 is controlled responsive to teletherapy management server 30 so as to position patient 100 immobilized to patient platform 90, and in particular target tissue of stage 1000, in relation to therapeutic agent source 20, responsive to the treatment plan of stage 1010, the precise positioning performed responsive to the derived synthetic scan, or scans, of stage 1050. Advantageously, positioning apparatus 80 is thus precisely controlled taking into account changes in target tissue positioning over the breathing cycle. In an embodiment wherein irradiation gating is performed, irradiation gating may thus be performed in accordance with any phase of the breathing cycle.

In stage 1070, target tissue deformation is identified responsive to a comparison of the synthetic scan, or scans, of stage 1050 and the other of the obtained pre-treatment scan of stage 1020 and the reference scan, or scans of stage 1000. The comparison and identification of changes is also known as a morphological analysis. In greater detail, in the event that the one or more computed motion vector fields have been performed on the pre-treatment scan of stage 1020 to create a synthetic scan whose phase is consonant with the treatment plan phase scan of stage 1000, or to create a plurality of synthetic scans with phases consonant with respective phases of the plurality of reference scans, the synthetic scan, or scans are compared with the respective reference scan. In the event that the one or more computed motion vector fields have been performed on one or more of the reference scans of stage 1000, such as on the treatment plan phase scan of stage 1010, to create a synthetic scan whose phase is consonant with the pre-treatment scan of stage 1020, or to create a plurality of synthetic scans whose phase is consonant with the pre-treatment scan of stage 1020, the synthetic scan, or scans are compared with the pre-treatment scan of stage 1020. In one embodiment this is performed by deformable registration methods. Preferably, the synthetic scan, or scans, of stage 1050 and the other of the obtained pre-treatment scan of stage 1020 and the respective reference stage 1000 are each displayed on display 60 with changes there between identified.

In stage 1080, the decision whether to introduce changes to the treatment plan of stage 1010 are in one embodiment determined by a physician or technician responsive to the morphological changes identified. In another embodiment teletherapy management server 30 automatically defines the need for changes to be introduced to the treatment plan, and displays calculated changes on display 60 for approval or override by authorized personnel. The decision on changing the treatment plan of stage 1010 is taken if the identified morphological changes alter the prescribed dose distribution defined in the treatment plan. Changing of the treatment plan of stage 1010 is also known as any of plan optimization, dose optimization, treatment optimization and treatment adaptation. The changes of treatment plan may include changes in the dose, irradiation angles, and respective position of the patient with regard to therapeutic agent source 20. The result of the treatment plan alteration is a new dose distribution at the target and critical organs consistent with the physician's prescription. An irradiation dose, or irradiation angle or location is thus adjusted responsive to the identified morphological changes. Changes to the treatment plan are preferably performed by optimization of the treatment plan dosage distribution responsive to the identified morphological changes.

As described above in relation to stage 1060, positioning apparatus 80 is arranged to position patient 100 immobilized to patient platform 90 to the appropriate position in relation to therapeutic agent source 20 responsive to the treatment plan and any changes thereto of stage 1080. In stage 1090, irradiation is performed responsive to the developed treatment plan of stage 1010, with any changes of stage 1080, by a signal transmitted by teletherapy management server 30 to therapeutic agent source 20 and positioning apparatus 80 with patient platform 90.

If the identified morphological changes of stage 1070 do not affect the dose distribution in the target and critical organs as prescribed in the treatment plan of stage 1010, the patient positioning and treatment is performed according to the treatment plan of stage 1010 and the patient positioning of stage 1060.

In one embodiment, irradiation is performed gated to the treatment plan phase, and thus morphological changes in respect to the treatment plan phase scan are preferably of particular interest in stages 1050-1070. In another embodiment, irradiation is performed over the entire breathing cycle, and thus morphological changes in respect to the entire breathing phase cycle are preferably of particular interest in stages 1050-1070.

The above has been described in an embodiment in which the treatment plan phase scan is used to identify morphological changes, however this is not meant to be limiting in any way. In another embodiment, the computed motion vector field is applied to the treatment plan phase scan, and morphological changes are identified by a comparison of an obtained synthetic treatment plan scan vectored to the phase of the obtained pre-treatment scan.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. A method of controlling irradiation positioning, the method comprising:
    obtaining a plurality of reference scans of a target tissue, each representing a unique phase of a breathing cycle;
    obtaining a pre-treatment scan of the target tissue;
    identifying the reference scan of the obtained plurality of reference scans whose phase is consonant with the obtained pre-treatment scan;
    computing at least one motion vector field between the identified reference scan and another of the plurality of reference scans different from the identified reference scan;
    applying the at least one computed motion vector field to one of the obtained pre-treatment scan and the another of the plurality of reference scans so as to derive at least one synthetic scan whose phase is consonant with the other of the obtained pre-treatment scan and the another of the plurality of reference scans; and
    positioning the target tissue in relation to a therapeutic agent source responsive to said obtained at least one synthetic scan.

2. The method of claim 1, further comprising:
    identifying morphological changes to the target tissue responsive to a comparison of the derived at least one synthetic scan with the other of the obtained pre-treatment scan and the another of the plurality of reference scans; and
    adjusting one of an irradiation dose, irradiation angle and irradiation positioning responsive to the identified morphological changes.

3. The method according to claim 2, wherein the at least one computed motion vector field comprises a plurality of motion vector fields, each of the plurality of motion vector fields associated with a particular one of the plurality of reference scans, and wherein a plurality of synthetic scans are derived by respectively applying each of the plurality of motion vector fields to one of the obtained pre-treatment scan and the respective one of the plurality of reference scans, and
    wherein said identifying morphological changes to the target tissue is responsive to a comparison of each of the plurality of derived synthetic scans with the respective other of the obtained pre-treatment scan and the respective one of the plurality of reference scans, to thereby identify morphological changes over the breathing cycle.

4. The method according to claim 1, wherein the another of the plurality of reference scans is a treatment plan phase scan.

5. The method according to claim 1, wherein the at least one computed motion vector field comprises a plurality of motion vector fields, each of the plurality of motion vector fields associated with a particular one of the plurality of reference scans, and wherein a plurality of synthetic scans are derived by respectively applying each of the plurality of motion vector fields to one of the obtained pre-treatment scan and the respective one of the plurality of reference scans.

6. A teletherapy control system comprising:
    a teletherapy management server;
    a positioning apparatus responsive to said teletherapy management server; and
    an imaging unit in communication with the teletherapy management server, said teletherapy management server arranged to:
    obtain a plurality of reference scans of a target tissue, each representing a unique phase of a breathing cycle;
    obtain a pre-treatment scan of the target tissue;
    identify the reference scan of the obtained plurality of reference scans whose phase is consonant with the obtained pre-treatment scan;
    compute at least one motion vector field between the identified reference scan and another of the plurality of reference scans different from the identified reference scan;
    apply the computed at least one motion vector field to one of the obtained pre-treatment scan and the another of the plurality of reference scans so as to derive at least one synthetic scan whose phase is consonant with the other of the obtained pre-treatment scan and the another of the plurality of reference scans; and
    control said positioning apparatus so as to position the target tissue in relation to a therapeutic agent source responsive to said derived at least one synthetic scan.

7. The teletherapy control system according to claim 6, further comprising a therapeutic agent source responsive to said teletherapy management server,
    wherein said teletherapy management server is further arranged to:
    identify morphological changes to the target tissue responsive to a comparison of the derived at least one synthetic scan with the other of the obtained pre-treatment scan and the another of the plurality of reference scans; and
    adjust one of an irradiation dose of said therapeutic agent source, irradiation angle from said therapeutic agent source and irradiation positioning relative to said therapeutic agent source responsive to the identified morphological changes.

8. The teletherapy control system according to claim 7,
    wherein the at least one computed motion vector field comprises a plurality of motion vector fields, each of the plurality of motion vector fields associated with a particular one of the plurality of reference scans, and wherein a plurality of synthetic scans are derived by respectively applying each of the plurality of motion vector fields to one of the obtained pre-treatment scan and the respective one of the plurality of reference scans, and
    wherein said identification of morphological changes to the target tissue is responsive to a comparison of each of the plurality of derived synthetic scans with the respective other of the obtained pre-treatment scan and the respective one of the plurality of reference scans, to thereby identify morphological changes over the breathing cycle.

9. The teletherapy control system according to claim 6, wherein the another of the plurality of reference scans is a treatment plan phase scan.

10. The teletherapy control system according to claim 6, wherein the at least one computed motion vector field comprises a plurality of motion vector fields, each of the plurality of motion vector fields associated with a particular one of the plurality of reference scans, and wherein a plurality of synthetic scans are derived by respectively applying each of the plurality of motion vector fields to one of the obtained pre-treatment scan and the respective one of the plurality of reference scans.

11. A non-transitory computer readable medium containing instructions for controlling an electronic device to perform a method of adjusting an irradiation treatment plan responsive to morphological changes, the method comprising:
  obtaining a plurality of reference scans of a target tissue each representing a unique phase of a breathing cycle;
  obtaining a pre-treatment scan of the target tissue;
  identifying the reference scan of the obtained plurality of reference scans whose phase is consonant with the obtained pre-treatment scan;
  computing at least one motion vector field between the identified reference scan and another of the plurality of reference scans different from the identified reference scan;
  applying the at least one computed motion vector field to one of the obtained pre-treatment scan and the another of the plurality of reference scans so as to derive at least one synthetic scan whose phase is consonant with the other of the obtained pre-treatment scan and the another of the plurality of reference scans; and
  positioning the target tissue in relation to a therapeutic agent source responsive to said obtained at least one synthetic scan.

12. The non-transitory computer readable medium according to claim 11, the method further comprising:
  identifying morphological changes to the target tissue responsive to a comparison of the obtained at least one synthetic scan with the other of the derived pre-treatment scan and the another of the plurality of reference scans; and
  adjusting one of an irradiation dose, irradiation angle and irradiation positioning responsive to the identified morphological changes.

13. The non-transitory computer readable medium according to claim 12, wherein the at least one computed motion vector field comprises a plurality of motion vector fields, each of the plurality of motion vector fields associated with a particular one of the plurality of reference scans, and
  wherein a plurality of synthetic scans are derived by respectively applying each of the plurality of motion vector fields to one of the obtained pre-treatment scan and the respective one of the plurality of reference scans, and
  wherein said identifying morphological changes to the target tissue of the method is responsive to a comparison of each of the plurality of derived synthetic scans with the respective other of the obtained pre-treatment scan and the respective one of the plurality of reference scans, to thereby identify morphological changes over the breathing cycle.

14. The non-transitory computer readable medium according to claim 11, wherein the another of the plurality of reference scans is a treatment plan phase scan.

15. The non-transitory computer readable medium according to claim 11, wherein the at least one computed motion vector field comprises a plurality of motion vector fields, each of the plurality of motion vector fields associated with a particular one of the plurality of reference scans, and wherein a plurality of synthetic scans are derived by respectively applying each of the plurality of motion vector fields to one of the obtained pre-treatment scan and the respective one of the plurality of reference scans.

* * * * *